US009572953B2

(12) United States Patent
Sliwa et al.

(10) Patent No.: US 9,572,953 B2
(45) Date of Patent: Feb. 21, 2017

(54) DEVICE HAVING AN ELECTROFORMED PLEATED REGION AND METHOD OF ITS MANUFACTURE

(75) Inventors: John W. Sliwa, Los Altos Hills, CA (US); Stephen A. Morse, Menlo Park, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1159 days.

(21) Appl. No.: 13/194,580

(22) Filed: Jul. 29, 2011

(65) Prior Publication Data

US 2012/0172843 A1 Jul. 5, 2012

Related U.S. Application Data

(60) Provisional application No. 61/428,790, filed on Dec. 30, 2010.

(51) Int. Cl.
*A61B 18/14* (2006.01)
*A61M 25/00* (2006.01)
(Continued)

(52) U.S. Cl.
CPC ........ *A61M 25/001* (2013.01); *A61B 18/1492* (2013.01); *A61M 25/008* (2013.01);
(Continued)

(58) Field of Classification Search
CPC ....... A61B 18/04; A61B 18/08; A61B 18/082; A61B 18/12; A61B 18/14; A61B 18/1402; A61B 18/149; A61B 18/1492; A61B 18/18; A61B 2018/08; A61B 2018/082; A61B 2018/14; A61B 2018/1405; A61B 2018/1435; A61B 2018/1437; A61B 2018/1465; A61B 2018/1475; A61B 2018/149; A61B 17/3415; A61M 25/0105; A61M 25/0069; C25D 1/02; C25D 1/08; C25D 5/02; C25D 5/10; C25D 5/18; C25D 5/54
(Continued)

(56) References Cited

U.S. PATENT DOCUMENTS 5,846,238 A * 12/1998 Jackson et al. ................ 606/41
5,899,898 A *  5/1999 Arless et al. .................. 606/22
(Continued)

*Primary Examiner* — Michael Peffley
*Assistant Examiner* — Khadijeh Vahdat
(74) *Attorney, Agent, or Firm* — Wiley Rein LLP

(57) ABSTRACT

A deflectable, flexible device includes an elongate body, a convoluted tip portion at a distal end of the elongate body, and a lumen to receive one or more wires. The convoluted tip portion includes an electroformed pleated region which is formed by electrodepositing a metal on a mandrel having a pleated region. The convoluted tip portion may be hermetically sealed to permit repeated sterilization. The electroformed pleated region may include one or more fluid emission orifices. The convoluted tip portion extends or bends in response to fluid pressure manipulation, contact with tissue, manipulation with an internal spring or wire, or by a user pushing, pulling, or twisting the catheter directly or via an introducer sheath or the like. The convoluted tip portion may further include an RF ablation element or other energy-driven technique to create continuous linear lesions or a sensing element.

14 Claims, 2 Drawing Sheets

(51) Int. Cl.
*A61M 25/01* (2006.01)
*C25D 1/00* (2006.01)

(52) U.S. Cl.
CPC .... *A61M 25/0074* (2013.01); *A61M 25/0133* (2013.01); *C25D 1/00* (2013.01); *A61M 25/0141* (2013.01); *A61M 25/0147* (2013.01); *A61M 25/0155* (2013.01); *A61M 25/0158* (2013.01)

(58) Field of Classification Search
USPC ......... 606/32, 34, 37, 39, 40, 41, 45, 47–50; 604/523, 528; 205/73
See application file for complete search history.

(56) References Cited

U.S. PATENT DOCUMENTS

| | | | |
|---|---|---|---|
| 6,719,723 B2* | 4/2004 | Werneth | 604/113 |
| 7,691,095 B2 | 4/2010 | Bednarek et al. | |
| 2002/0087208 A1* | 7/2002 | Koblish et al. | 607/113 |
| 2003/0055416 A1* | 3/2003 | Damasco | A61B 18/02 606/21 |
| 2005/0075630 A1* | 4/2005 | Truckai et al. | 606/41 |
| 2005/0228372 A1* | 10/2005 | Truckai | A61B 18/14 606/41 |
| 2007/0167941 A1* | 7/2007 | Hamel et al. | 606/34 |
| 2010/0286684 A1* | 11/2010 | Hata et al. | 606/33 |

\* cited by examiner

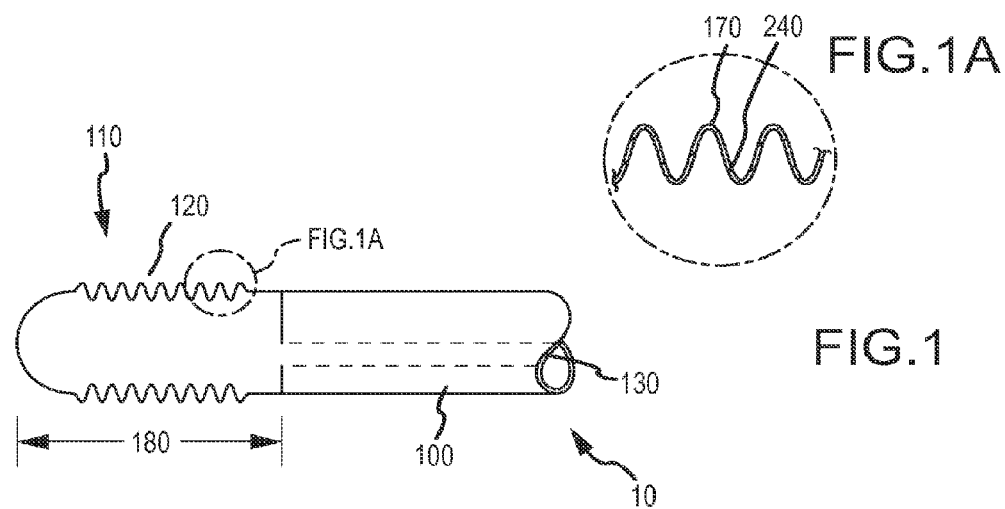
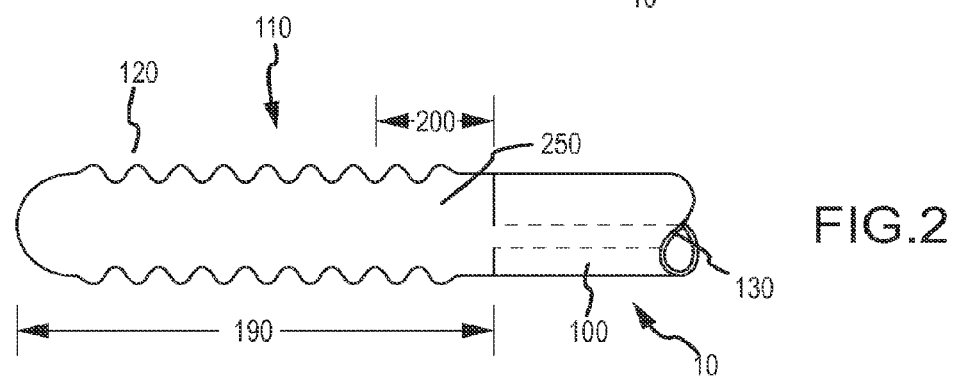
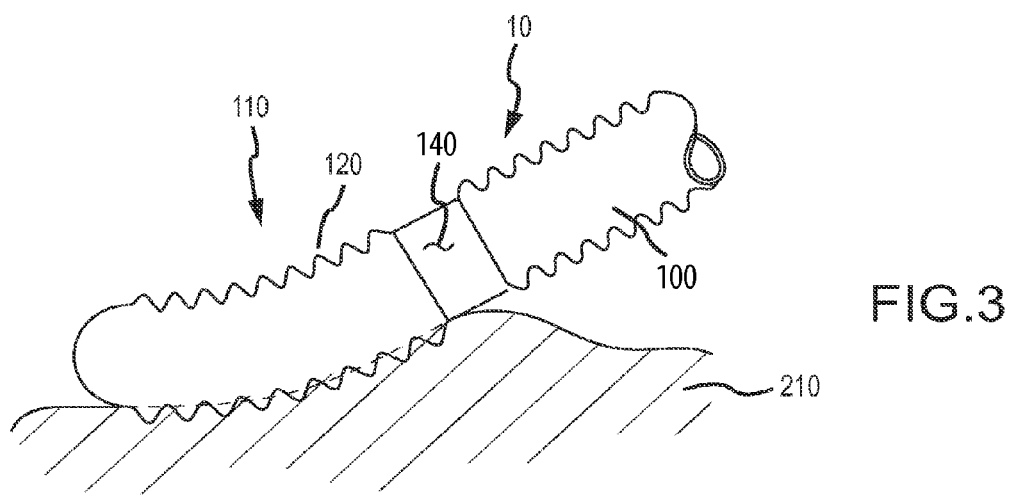

DEVICE HAVING AN ELECTROFORMED PLEATED REGION AND METHOD OF ITS MANUFACTURE

CROSS-REFERENCE TO RELATED APPLICATIONS

This application claims the benefit of and priority to U.S. provisional patent application No. 61/428,790, filed 30 Dec. 2010, which is hereby incorporated by reference as though fully set forth herein.

BACKGROUND OF THE INVENTION a. Field of the Invention

The instant disclosure relates to deflectable and steerable elongate devices, such as medical catheters. In particular, the instant disclosure relates to a family of such devices having portions formed using electroforming techniques, including bendable and stretchable pleated or bellows-like regions, partial and entire shaft portions, and the like.

b. Background Art

Deflectable and steerable elongate devices such as catheters are used for an ever-growing number of medical, industrial, and manufacturing procedures. For example, in the case of the former, catheters are used for diagnostic, therapeutic, and ablative procedures, to name just a few examples. A catheter can be manipulated through a patient's vasculature to a portion of targeted tissue or other intended site, for example, a site within or near the patient's heart or other organ or location within a body. A catheter typically carries one or more energy emitting elements (e.g., electrodes, hyperthermic ablation elements, cryogenic elements, etc.), which may be used for tissue ablation, diagnosis, or the like. Some catheters perform only passive or diagnostic functions such as sensing the electrical waveforms of a beating heart.

An important aspect of any catheter procedure is good contact between the catheter and the targeted tissue of an organ or other location in the body. Accordingly, it is desirable for a catheter to have a flexible tip portion such that the catheter can bend and increase its contact area to tissue.

BRIEF SUMMARY OF THE INVENTION

It is desirable, therefore, to provide a family of deflectable or steerable and flexible devices such as medical catheters that both advantageously reduce the possibility of tissue perforation and better conform to tissue due at least in part to specific flexible shaft segments or other portions (e.g., a flexible tip portion and/or shaft) formed via electroforming techniques alone or in combination with other fabrication techniques, materials, and components.

It is also desirable to provide a catheter that is readily sterilizable for multiple uses.

It is also desirable to provide a catheter having a controlled variable length usable for ablating, diagnostic sensing, or other desirable applications.

It is therefore an object of the present disclosure to provide a family of catheters with a flexible shaft and/or tip portion that can bend and/or deform and increase their contact area to tissue (and reverse such bending or deformation via manual or robotic control input, for example).

Another object of the present disclosure is to provide a catheter whose ablative length can be varied.

Yet another object of the present disclosure is to provide a catheter that can be repeatedly reused and sterilized, within an engineered use-limit, without harming the structural integrity of the catheter or endangering patients.

In one embodiment, a catheter includes an elongate body, a convoluted tip portion at a distal end of the elongate body, and at least one lumen. The convoluted tip portion includes an electroformed regular or irregular corrugated, creased, ridged, bellows-like or pleated region (herein in the plural form "pleated" or in the singular form "pleat"). The electroformed pleated region can have a tapered diameter along its length or can be angled relative to the tip axis. The electroformed pleated region can include at least one fluid emission orifice which can be laser drilled. The electroformed pleated region can be over coated with a noble metal or alloy or other biocompatible material. The pleats provide an improved bending or extensional behavior of the region relative to that of an equivalent unpleated region. Such pleats are typically multiple in nature, with each pleat offering increased flexural freedom such as for bending or axial compression/extension.

Pleats may also offer improved crush-resistance or kink-resistance. Pleats may be any designed undulation or shaping of the shell walls and can be implemented by electroforming, which may favorably improve bending and/or extension behavior or avoid buckling behavior.

In another aspect, the convoluted tip portion and/or the elongate body can be hermetically sealed. In some embodiments the convoluted tip portion can include a non-round cross-section. Optionally, the elongate body can include an acoustically transmissive window or a window for an optical sensor.

In another embodiment of the present disclosure, the convoluted tip portion further includes one or more RF ablation elements. The RF ablation element may be hermetically sealed and may or may not itself be pleated or formed out of electroformed material.

In yet another aspect of the present disclosure, a method of manufacturing a catheter includes the steps of forming an electroformed pleated region, obtaining a catheter shaft, and securing the electroformed pleated region to the catheter shaft. The step of forming an electroformed pleated region further includes the steps of providing a mandrel having a pleated region, depositing (e.g., electroforming) a metal onto the mandrel, trimming the mandrel, and dissolving the mandrel, thereby forming an electroformed pleated region. The step of depositing a metal onto the mandrel can include depositing an electroformable metal such as nickel, copper or gold onto the mandrel. The method can further include the step of over coating the electroformed pleated region (or, optionally, any unpleated electroformed region) with a gold, rhodium or platinum alloy.

In a further embodiment of the present disclosure, a tissue ablation system includes an RF ablation catheter having an elongate body, a convoluted tip portion having an electroformed pleated region, and one or more fluid chambers located adjacent to or within the electroformed pleated region. When the fluid chamber(s) is forcefully filled or forcefully evacuated, the fluid exerts a force to deform the convoluted tip portion. This hydraulic deformation can result in a useful bending or change in length of the convoluted tip portion. In lieu of hydraulic actuation in certain embodiments, pneumatic actuation may be implemented (e.g., carbon dioxide gas or the like), with consideration given to the nature of the relevant medical applications or procedures.

In a further embodiment of the present disclosure, a tissue ablation system includes a catheter having an elongate body, a convoluted tip portion having an electroformed pleated region, and a mechanism for deflecting the distal end of the elongate body. An example of a mechanism for deflecting the distal end of the elongate body can be seen generally by reference to U.S. application Ser. No. 11/023,667, filed 28 Dec. 2004, now U.S. Pat. No. 7,691,095, owned by the common assignee of the present disclosure, and hereby incorporated by reference in its entirety. Another technique for deflecting or steering a catheter according to the instant disclosure involves deployment of the catheter via a deflectable introducer or sheath at least as to the majority of shaft portion disposed within such an introducer (e.g., the AGILIS introducer designed, manufactured, and distributed by St. Jude Medical, Inc. of Little Canada, Minn.).

An advantage of the present disclosure is that it offers readily reversible bending and extensional catheter tip and/or shaft flexibility while also providing hermeticity or a sealed tip/body.

Another advantage of the present disclosure is that it provides a multi-length catheter tip whose ablative or sensing electrode length can be varied in-vivo.

Yet another advantage of the present disclosure is that it provides a catheter having superb electrical shielding, kink-resistance, and torque properties.

A further advantage of the present disclosure is that it provides a catheter which can be repeatedly reused and sterilized, within the constraints of a predefined number of safe uses, without affecting its handling properties.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 1 is a cross-sectional view of a catheter having a convoluted tip portion according to an embodiment of the present disclosure.

FIG. 1A is a break-out view of an electroformed pleated region according to an embodiment of the present disclosure.

FIG. 2 illustrates a lengthwise extension of the convoluted tip portion according to an embodiment of the present disclosure.

FIG. 3 illustrates a convoluted tip portion according to an embodiment of the present disclosure bent or radiused against a tissue.

DETAILED DESCRIPTION OF THE INVENTION

Figure 4:
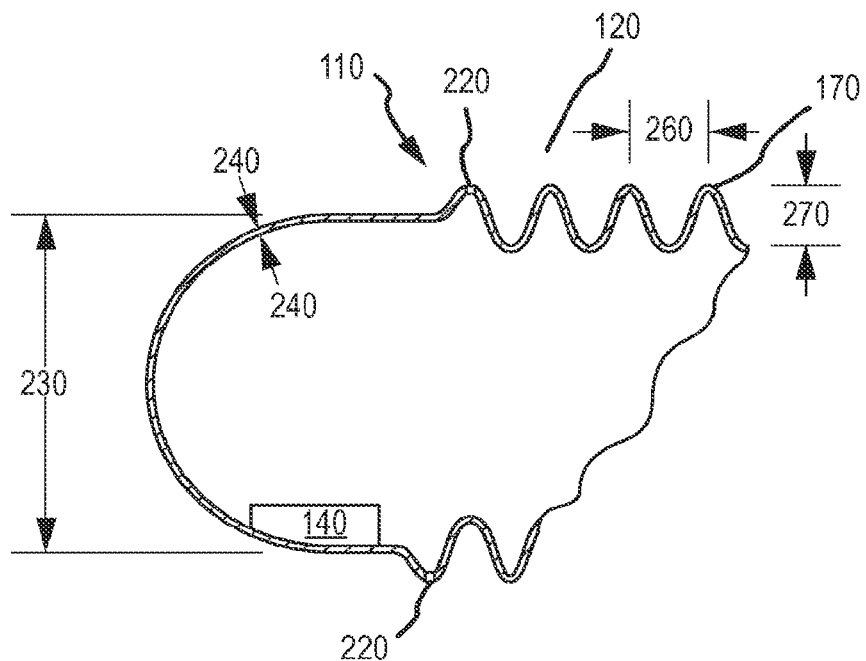
FIG. 4 illustrates an electroformed pleated region having laser-drilled orifices according to an embodiment of the present disclosure.

The present disclosure provides a family of catheters having an electroformed pleated region in the catheter tip portion that is desirably and advantageously adapted to better conform to tissue and reduce perforations. The present disclosure also provides reusable catheters wherein reuse is made possible by replacing conventionally employed polymeric lumen bodies with hermetic electroformed lumen bodies. The disclosure also provides a variety of methods of manufacturing a family of catheters with an electroformed pleated region and a tissue ablation system utilizing a catheter with an electroformed pleated region.

Referring now to the drawings, and in particular to FIG. 1, a catheter 10 includes an elongate body 100 having a convoluted tip portion 110 with a length 180 at its distal end. Body 100 also defines a lumen 130 (shown in phantom), which will be familiar to the ordinary artisan.

Lumen 130 can, for example, be configured to permit catheter 10 to be advanced through a patient's vasculature over a guide wire. Alternatively, one or more steering wires (also commonly referred to as pull wires) can be routed through lumens such as 130. Lumen 130 can also provide a passageway for electrical leads and/or signal wires. Lumen 130 can also be adapted to receive one or more of an optical conduit, a fluid, or a medical device. Such a fluid could be used for irrigation, tip-cooling, tissue cooling or even for hydraulic distortion of one or more pleated regions such as a tip or an entire pleated catheter tip plus body. Of course, it should be understood that the present invention is not limited to catheters having a single lumen 130, and that catheter 10 can have multiple such lumens without departing from the spirit and scope of this disclosure. That is, in certain aspects, catheter 10 includes multiple lumens, each of which may serve the same or a different purpose than one or more other lumens (e.g., multiple fluid lumens, one fluid lumen and one lumen for passing a medical device, and any other combination of lumens).

The catheter 10 can have axisymmetric or asymmetric handling properties. In general, catheter 10 can include one or more features that will be familiar to those of ordinary skill in the art, such as embedded pull wires, braided reinforcing layers, and the like. Accordingly, the construction of catheter 10 will not be further described herein except to the extent necessary to understand the present disclosure.

In some aspects, the convoluted tip portion 110 may be a mating part secured, for example by an adhesive or a snap-fit connection, to elongate body 100. Alternatively, the convoluted tip portion 110 may be integrally formed with elongate body 100 such that the entire extended catheter 10, including the elongate body 100, convoluted tip portion 110, and length 180, is all electroformed. Although known push/pull or twisting control wires may be used to distort one or more pleated regions of the inventive catheters, for example a pleated tip or a full-length pleated catheter, the inventors also anticipate the use of liquid hydraulics or pneumatic gas pressure as applied through one or more pressurization lumens to distort the catheter tip and/or body. Specifically, in one preferred embodiment, the pleated catheter portion enwraps a polymeric-based multilumen tube. The interior flexible multilumen tube has multiple isolated fluid passages off of its central axis such that pressurization of an outboard lumen causes stretching/compression or bending of a pleated catheter section. The interior multilumen tube can also be employed as a nondisposable incorporated mandrel for use in electroforming portions of catheter 10 as disclosed herein. For example, the polymeric multilumen tube may be rendered plateable, such as by placement of a sputtered/ion-deposited metal film or an electroless nickel plate "seed" coating. The multilumen tube mandrel can then be left in the electroform permanently, rather than dissolving it as described herein.

In other aspects the convoluted tip portion 110 can provide a window region for a sensor or other device disposed within tip 110 or routed through lumen 130. For example, an optical sensor may be disposed within tip 110, and an optically-transparent window can be provided to facilitate use thereof. Similarly, the convoluted tip portion 110 can include an acoustic window, which permits the transmission of acoustic energy from an acoustic (e.g., ultrasound) transducer disposed within tip 110 and oriented to emit and receive acoustic energy through the acoustic window. One of ordinary skill would readily appreciate how such sensors and other devices may be installed or otherwise disposed in tip 110 or routed through or passed through lumen 130. Ceramic or glass windows for allowing such ingoing/outgoing sensor energies may be brazed or soldered into the electroformed shell thus preserving absolute hermeticity.

The convoluted tip portion 110 includes an electroformed pleated region 120. The electroformed pleated region 120 can have an overall average varying shape, such as straight and cylindrical, tapered or of stepped diameter along its length. Alternately, the electroformed pleated region 120 can have a constant average diameter along its length. In another aspect, the electroformed pleated region 120 can have a cross-section which is, at least in part, nonround such as polygonal or oval. The pleated region provides bendability and/or extendability in one or more directions. Such motions may be employed, for example, in gaining improved access through vasculature, in placing the catheter tip in a more beneficial tissue-contact state, or even for cyclically scanning the tip such as to achieve a scanning motion for a sensor or imaging transducer in the tip.

Electroforming upon a shaped sacrificial mandrel, sometimes also referred to as electrodeposition, which is described further below, allows pleated region 120 to offer numerous advantages. For example, electroformed pleated region 120 can act as an adjustable-length electrical conductor for a useful medical purpose, such as for use as a variable-length ablation electrode or electrode for sensing electrical activity (e.g., cardiac electrograms) or for pacing the heart. Of course, electroformed pleated region 120 offers other advantages as well. For example, electroformed pleated region 120 can provide safety advantages such as bendability, extendability, and compressibility to avoid tissue perforations while at the same time encouraging intimate tissue contact. The electroformed pleated region 120 also provides improved crush-resistance and kink/buckling resistance. Likewise, electroformed pleated region 120 can provide electromagnetic shielding against interference for incoming and/or outgoing signals. Additionally, if electroformed pleated region 120 includes nickel deposits, it could be manipulated utilizing magnetic steering systems, such as the Niobe Remote Magnetic Navigation System from Stereotaxis, Inc. of St. Louis, Mo. or the magnetically-controlled catheter systems of Magnetecs Corporation of Los Angeles, Calif.

The electroformed pleated region 120 is formed by a plurality of individual pleats 170. These pleats 170 can be integrally formed, or, alternatively, can be formed as a plurality of segments that are metallurgically joined (e.g., by laser welding). A break-out view of electroformed pleated region showing individual pleats 170 with a thickness 240 is depicted in FIG. 1A. A thickness 240 of the electroformed pleats may for example be in the range of about 0.001 to about 0.006 inches. In one preferred embodiment, the electroformed pleated region 120 is fabricated by electroforming all of the pleats as a pleated body on a common mandrel wherein no individual pleat-joining is then later required.

The individual pleats 170 can be arranged at angles to each other, which can desirably impart direction-biased bending and extensional capability to electroformed pleated region 120. Pleats 170 also advantageously increase the radiopacity of the convoluted tip portion 110. Additionally, the individual pleats 170 desirably increase the resistance of electroformed pleated region 120 to buckling and/or collapse in comparison to a non-pleated electroformed structure. Another advantage is that individual pleats 170 act to provide a favorable contact impedance or resistance to tissue by assuring multiple parallel electrical contacts to tissue. Still another advantage is that the individual pleats 170 atraumatically enhance tissue gripping, while being shaped to minimize the likelihood of pinching or grabbing tissue relative to certain extant devices. One of skill in the art would recognize the pleated tips of the invention as corrugated (pleated) thin-walled shell structures whose respective pleats or corrugations can have varying size, shape, depth, pattern, thickness, and number that essentially determine the overall bendability, extendability, kink resistance, crush resistance and torqueability of the overall structure and portions thereof in conjunction with any of a variety of deflection schemes including mechanical, hydraulic, pneumatic and the like.

One suitable method of forming electroformed pleated region 120 is as follows. First, a sacrificial mandrel having a pleated region is provided. Next, an electroformable metal is deposited (e.g., electroformed from a chemical bath) onto the mandrel. One known suitable electroformable metal is electrodeposited nickel. One of skill in the art will appreciate that the wall thickness 240 of the electroformed pleated region 120 is determined by the thickness or amount of deposited electroformed metal. Once the metal has been deposited onto the mandrel, the mandrel is typically trimmed and dissolved. In the case of electrodeposited or electroformed nickel, a dissolvable preshaped (pleated) aluminum mandrel may be sacrificed. Aluminum mandrels are convenient because they can be easily shaped and easily dissolved, and they are electrically conductive for electroforming thereon. If a material other than a metal is employed for the mandrel (note the multilumen polymeric mandrel example described above) then it must be rendered at least surface conductive first as by a deposited metal thinfilm or electroless plated thinfilm metal. Then the thinly metal coated polymeric mandrel can be electroformed upon. A polymeric mandrel can be extruded or even molded with a variety of favorable undulating or pleated shapes. As described above, such a polymeric mandrel can remain in the electroformed catheter as an integral design element and can itself be formed, molded or extruded to have the desired pleated shape. The mandrel may take any of a plurality of shapes, which can be selected according to the intended or desired use of the resulting electroformed pleated region. Optionally, the electroformed pleated region 120 can be over coated with a noble metal or alloy such as gold or a gold alloy, or platinum or a platinum alloy for biocompatibility or enhanced tissue-contact properties. Electroforming techniques such as those described by Precision Manufacturing Group, LLC in relation to its Servometer® division product and service offerings can also be used in connection with the present disclosure.

The electroformed pleated region 120 can be hermetically sealed if desired since the electroformed metal shell is itself inherently hermetic, in contrast to polymer materials often used in catheter construction. In another aspect, the elongate body 100 or the entire catheter 10 can be hermetically sealed, such as by forming it all out of electroformed (e.g. nickel) material without any joining metal/polymer seams. If a seam or joint is necessary it can be a metal/ceramic/metal joint which is soldered for example. Hermetic sealing permits the catheter 10 to be sterilized without damage such as by wet methods, gaseous (ETO) methods or even steam autoclaving. This offers an advantage over the prior art, for example because polymeric materials often admit some liquid and/or gaseous sterilant via bulk diffusion. The liquid and/or gaseous sterilant attacks features of the catheter interior such as conductor wires, which may result in degradation of the polymeric shaft and/or lumen construction materials themselves. Gamma sterilization would also be more benign if the catheter is fabricated of electroformed metal rather than of polymers susceptible to gamma embrittlement. Hermetic sealing of the catheter also prevents internal water deposits due to condensation from sterilization procedures such as steam autoclaving. The ability of catheter 10 to undergo sterilization (e.g., autoclaving, wet immersion sterilization, plasma sterilization) without damage or degradation is particularly desirable, insofar as extant polymeric catheters can degrade after even a single sterilization cycle.

Thus, catheter 10 according to the instant disclosure can be labeled for a specified engineered safe number of multiple uses, or, alternatively, can have enforced disposability after a specified number of safe engineered multiple uses, making catheter 10 a more economical choice for practitioners. "Enforced disposability" means that the catheter cannot safely be used after a certain number of uses, and may be provided in any suitable fashion. In certain aspects, enforced disposability is provided by including an integrated circuit ("IC") chip, such as in the handle or connector, that stores and reports (e.g., to other components of a tissue ablation system) how many times catheter 10 has been used and allows such use up to a preset number of uses (e.g., by preventing the tissue ablation system from activating if the preset number of uses has been exceeded). Of course, catheter 10 can also be disposable or disposed of after a single use without departing from the present teachings.

FIG. 2 illustrates a lengthwise (stretched) extension of the convoluted tip portion 110 of FIG. 1 according to an embodiment of the present disclosure. As depicted in FIG. 2, the convoluted tip portion 110 can be extended to a length 190 that is greater in length than the undisturbed (e.g., as-electroformed) length 180. Similarly, in another aspect, convoluted tip portion 110 can be shortened (e.g., compressed) to a length 200 that is shorter in length than the undisturbed length 180 as by applying a negative pressure (suction) to a liquid filled electroformed tip fluid chamber. Advantageously, the catheter 10 can be advanced or retracted from a lumen or blood chamber by using this lengthwise deformability of the tip or of the tip/lumen body. As the tip length 200 is compressed or stretched, the pleats are forced closer together or further apart, with each pleat acting like a small spring.

The extension or contraction in length of convoluted tip portion 110 described above can be effected in any suitable manner. For example, in some embodiments, internal fluid pressure is used to effect the change in length. That is, a positive pressure can be created in a fluid chamber 250 located adjacent to or in the electroformed pleated region 120 (e.g., by filling fluid chamber 250 with a pressurized fluid, such as saline) to extend the length of convoluted tip portion 110, while a negative pressure can be created in fluid chamber 250 (e.g., by evacuating (applying suction negative pressure to) fluid chamber 250) to contract the length of convoluted tip portion 110. Examples of fluids may be liquids such as saline or gases such as biocompatible carbon dioxide. As previously noted, by providing multiple off-axis pressurization lumens one could, by selective or differential pressurization, achieve bending of a pleated section. Some electroformed shapes will also encourage deformation along a direction or axis of least elastic resistance such as via a rotational torque deformation.

In other aspects of the disclosure, the lengthwise extension or contraction of convoluted tip portion can be caused by contact with tissue, an internal spring or wire, or by a user pushing, pulling, twisting, or otherwise manipulating the catheter. In one aspect the convoluted tip portion 110 bends as it comes into contact with tissue. The bending of convoluted tip portion 110 causes part of the convoluted tip portion 110 to extend while causing another opposed portion of the convoluted tip portion 110 to contract. One of ordinary skill in the art would appreciate that the pleats or corrugations may have different sizes, arrangements and distributions depending on the catheter distortions and/or flexibility desired. In general the electroformed metal thickness 240 is small in comparison to the dimensions of the pleats (pitch, height, radius, etc.) themselves. Pleats for promoting bending and stretching may be of any shape which encourage deformation at reduced loading (i.e. makes the part more easily deformable than the unpleated electroformed form). Pleats could, for example, be generally triangular, radiused, round, polygonal, square or rectangular. They may be stacked and independent of each other or they may be continuous in the case of their being screw-thread or helical in shape. They may occur in groups or even singly. They may have various orientations to the local catheter/lumen central axis. Their spacing, shape and/or size may systematically vary with distance or position on the electroform. Their stiffness behavior may be modeled using 3D CAD programs or simulators.

FIG. 3 illustrates that the convoluted tip portion 110 can further act as or physically include one or more RF ablation elements. Likewise, the elongate body 100 can include a catheter control handle at its proximal end (not shown). Advantageously, the adjustable length of the RF ablation element in FIG. 3 comprises all of pleated section 120. Thus, the catheter 10 can be readily used for sensing, mapping, pacing, or ablating. Moreover, the variability of the length of RF ablation element and its bending flexibility desirably permit long and continuous curved or straight lesions.

In one embodiment of the invention, the insulating spacer 140 of FIG. 3 is a ceramic spacer which electrically isolates the pleated electrode tip 110 from the rest of the pleated catheter shaft 100. This allows for ablation only from the tip portion. The insulating spacer 140 can include an alumina cylinder having through-holes or lumens for wiring and having selectively-placed external metallization for solder joining to the adjacent electroformed tip 110 and shaft 100. An electroformed flexible tip can have both superior bendability and tissue-conformance but also have its ablative-length changeable as by the aforementioned pressurizations. Note that the entire catheter of FIG. 3 is inherently hermetic and sealed.

FIG. 3 also illustrates a convoluted tip portion 110 according to an embodiment of the present disclosure that is bent or radiused against a heart or myocardial tissue 210. The bending of the convoluted tip portion 110 can be effectuated in any suitable manner, including the ways described above with respect to lengthwise extension or contraction of convoluted tip portion 110. The bending of the convoluted tip portion 110 offers numerous advantages, including better contact with tissue and less likelihood of tissue perforations, enhanced antisliding resistance, reduced electrical impedance, and superior heat removal. Elongate body 100 can also be bendable (or even extendable) as depicted by its own smaller pleats as shown. In one aspect the tip 110 is bendable by the forces imposed on it by when brought into contact with tissue. Bendability of the tip 110 (or even of an electroformed body-lumen) can be achieved through mechanisms such as pull wires or the pressurization/differential pressurization of off-axis fluid lumens. Lumens employed for fluidic or pneumatic pressurization to achieve favorable electroform distortion may or may not be independent of any employed for cooling or irrigation.

The pleated shaft 100 as illustrated in FIG. 3 may have a pleat pitch of about 2.5 mm, with a large pitch to height ratio. A greater pitch to height ratio provides for a structurally stiffer catheter shaft 100, i.e. one that is flexible but can be maneuvered by pushing and pulling. One of ordinary skill in the art would appreciate that by varying the pleat shapes and dimensions along the tip/shaft that any desired stiffness requirement can be met without changing the tip/shaft material. This allows, for example, the creation of preferred stiffness profile catheter products for specific customers.

Typically the electrodeposited or electroformed metal thickness will be a few mils or thousandths of an inch. For example, typical thicknesses would be between 1 mil (0.001 inch or 25.4 microns) and 7 mils (0.007 inch or about 178 microns). The pleat pitch and pleat height would typically be significantly larger as shown in the figures—thus providing a thin-walled or shell-like pleated object whose flexure behavior is dominated by the "thin flexible" pleats. Pleat pitches and heights will commonly be many times the electrodeposit thickness, e.g., 2-20× and probably more commonly 4-8×.

FIG. 4 illustrates a tissue ablation system according to an embodiment of the present disclosure. A catheter includes a convoluted tip portion 110 having an average diameter 230. The convoluted tip portion 110 comprises an electroformed pleated region 120, an RF ablation element, and fluid emission orifices 220. The electroformed pleated region 120 includes individual pleats 170 with an axial pitch 260, a total radial height 270, a thickness 240, and an average diameter 230. Axial pitch 260 and radial height 270 can be optimized so that desired flexibility, stiffness, torque transmission, and extensional properties can be achieved. One of skill in the art will appreciate that the bending, torque, and extensional properties of the electroformed pleated region 120 (or the more mildly pleated shaft 100 of FIG. 3) will be determined largely by the ratio of axial pitch 260 to radial height 270, the number of individual pleats 170, and the ratio of radial height 270 to diameter 230, or the ratio of radial height 270/diameter 230 and thickness 240.

In one aspect, the individual pleats 170 vary in shape, size, and/or configuration along the length of the electroformed pleated region 120 to provide variations in certain properties of catheter 10 (e.g., increased flexibility of the catheter). For example, each individual pleat 170 can comprise an axial pitch 260 and a radial height 270 that can be the same or different from other individual pleats 170. The pleats 170 may be joined by corners having controlled radii as shown in the Figures. Pleats 170 may have one of a plurality of shapes such as the illustrated sawtooth or sine wave, round ribs, etc. Additionally, the pleats 170 may be singly stacked as shown or may form continuous or discontinuous spirals and the like.

In one embodiment of the invention, the electroformed thickness 240 per the above comments on thickness will typically be significantly less than a pleat pitch, width or height such that a flexible membrane is provided which can be treated as a curvilinear or corrugated elastic shell. In a preferred embodiment, the thickness 240 will be in the range of about 0.001 to about 0.007 inches such that local portions are elastic and easily bendable. The pleat pitch and height will be larger than the thickness 240 and preferably of the same order of magnitude as each other (e.g. both within the above 4-8× ratio range for example). For example, a specific ablation tip may have an electroformed thickness of about 2 mils (0.002 inch or about 50 microns), a pleat pitch of 12 mils (0.012 inch or about 305 microns) and a pleat height of 10 mils (0.010 inch or about 254 microns) and an average tip diameter of 8 French or 8/Pi=2.548 mm or about 2548 microns. In such embodiments, the tip has pleat features which occupy about (254×2)/2548 or 0.20 or 20% of the average diameter as roughly shown in FIGS. 1 and 2.

Irrigant fluid emission orifices 220 shown in FIG. 4 can be laser drilled. Laser drilling is particularly advantageous, as the laser drilled holes can be drilled anywhere in the electroformed pleated region 120 and can thus jet fluid in almost any direction since pleat faces may be directed in numerous directions. Alternately, the fluid emission orifices can have their flow directed radial to the catheter 10 or convoluted tip portion 110 axis. In yet another embodiment, the fluid emission orifices can have their flow directed at an angle to the catheter 10 or convoluted tip portion 110 axis. In another embodiment, the shaft 100 comprises saline lumens running up and down the shaft 100 that provide a closed, circulating cooling scheme. In yet another embodiment of the invention, the irrigant is expelled from the shaft 100.

Figure 5:
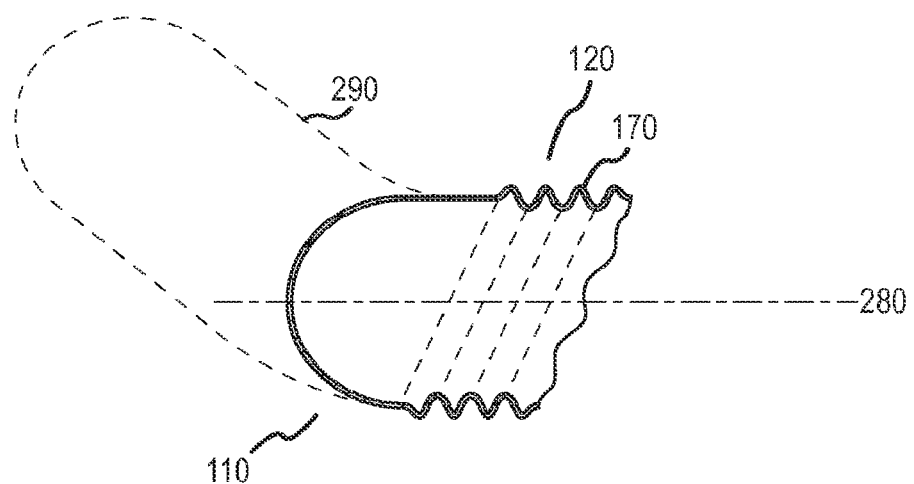
FIG. 5 depicts a convoluted tip portion having an angled pleated region according to an embodiment of the present disclosure.

FIG. 5 depicts a convoluted tip portion 110 having an electroformed pleated region 120 according to an embodiment of the present disclosure. In this embodiment, the electroformed pleated region 120 comprises individual pleats 170 that are angled relative to the tip axis 280. These may form a spiral or simply a stack of tilted yet parallel pleats (shown). Thus, upon fluid pressurization or wire-push extension, the convoluted tip portion 110 extends in an angled direction 290 Additional sculpturing or hole-drilling of the inventive tips as by laser cutting of electro-discharge machine ("EDM") is yet another embodiment of the invention.

Although several embodiments of this disclosure have been described above with a certain degree of particularity, those skilled in the art could make numerous alterations to the disclosed embodiments without departing from the spirit or scope of this invention. For example, though the disclosure describes only a single electroformed pleated region 120, one of ordinary skill in the art can envision that a catheter 10 could comprise more than one electroformed pleated region 120 in a tip. For instance, the catheter 10 could comprise a first highly flexible pleated region 120 in the tip and a second, less flexible pleated region 120 in (or as) the catheter body.

As another example, a person of skill in the art could incorporate multiple sensors, electrodes, and/or transducers in the catheter body to better visualize or ascertain the content or behavior of various tissue structures. Likewise, one or more catheter tracking elements can be coupled to or formed within a portion of a catheter so that a system employing non-ionizing radiation can be used to locate the catheter during a procedure or working condition. Examples of such systems include the EnSite System from St. Jude Medical, Inc. of Little Canada, Minn. and the CARTO system from Biosense Webster, Inc. of Diamond Bar, Calif. These systems utilize either catheter tip electric field positioning (former) or catheter tip magnetic field positioning (latter). As still another example, one of ordinary skill in the art will appreciate that a metallic or pleated convoluted shaft also has superb electrical shielding properties such as for high-sensitivity waveform detection. This is true even in unpleated yet electroformed regions.

In some embodiments, the catheter tip is disposable, but the lumen/body/handle component is not disposable, i.e. they are separable by a connector or coupling. Such could be achieved by having a positive-locking sealing connector between disposable and nondisposable sections. Alternatively, the tip may be reuseable, the lumen/body/handle may be disposable, and at least one of the tip and/or lumen/body are electroformed and pleated.

The invention may be used to provide individual practitioners with individually customized catheter behaviors such as by using custom electrodeposition mandrels for each doctor. These catheters may be disposable or controlled-reuseable depending on design and cost.

The novel use of a polymeric extrusion or polymeric molded entity as an electroforming mandrel has been described above. In such embodiments, such as where the entity has lumens, the polymeric "mandrel" may permanently remain a part of the catheter thereby avoiding the traditional electroforming step of dissolving the mandrel. In such cases, the electroformed shell is permanently bonded to the polymeric liner (mandrel), because electroforming was done on a thin-film metalized polymer mandrel. The mechanical properties of the catheter may be varied both by changing electroformed dimensions/shapes but also by changing polymer dimensions/shapes and even materials. Such a polymeric core might also be a highly deformable foamed material such as a closed-cell foam.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A device comprising:
   an elongate body, wherein the elongate body has a longitudinal axis;
   a variable length tip portion at a distal end of the elongate body,
   wherein the variable length tip portion comprises a first elastically deformable electroformed pleated region and the elongate body comprises a second elastically deformable electroformed pleated region, wherein the first and second elastically deformable electroformed pleated regions comprise adjacent pleats that extend perpendicularly to the longitudinal axis, such that the first and second elastically deformable electroformed pleated regions expand axially, and further wherein the first and second elastically deformable electroformed pleated regions are capable of being extended to a length that is greater than the undisturbed length; and
   at least one lumen;
   wherein the first elastically deformable electroformed pleated region further comprises at least one ablation element, and wherein the first elastically deformable electroformed pleated region in the variable length tip portion is more flexible than the second elastically deformable electroformed pleated region in the elongate body.

2. The device according to claim 1, wherein the first elastically deformable electroformed pleated region further comprises at least one fluid emission orifice.

3. The device according to claim 2, wherein the at least one fluid emission orifice is laser drilled or electro-discharge machined.

4. The device according to claim 1, wherein the first and/or second elastically deformable electroformed pleated region is capable of extension by internal pressure.

5. The device according to claim 1 wherein the at least one ablation element is a radiofrequency (RF) ablation element, and the RF ablation element is hermetically sealed.

6. The device according to claim 1, wherein the first and/or second elastically deformable electroformed pleated region has a tapered diameter along its longitudinal axis.

7. The device according to claim 1, wherein at least one of the adjacent pleats of the first or second electrically deformable electroformed pleated regions is oriented at an angle between 0 and 90 degrees to the longitudinal axis of the tip portion.

8. The device according to claim 1, wherein the first elastically deformable electroformed pleated region further comprises a non-round cross-section.

9. The device according to claim 1, wherein the elongate body further comprises at least one fluid lumen.

10. The device according to claim 9, wherein the elongate body further comprises at least one fluid emission orifice.

11. A deformable device, comprising:
    a radiofrequency (RF) ablation catheter having an elongate body comprising a first elastically deformable electroformed pleated region and an elastically deformable convoluted tip portion, wherein the elastically deformable convoluted tip portion comprises a second electroformed pleated region, wherein the first and second elastically deformable electroformed pleated regions comprise adjacent pleats;
    a fluid chamber adjacent to the second electroformed pleated region, wherein, the fluid chamber is capable of being pressurized with a fluid, and further wherein the fluid is capable of deforming the elastically deformable convoluted tip portion; and
    wherein the second elastically deformable electroformed pleated region is more flexible than the first elastically deformable electroformed pleated region.

12. The device according to claim 11, wherein the deformation is configured to result in a bending of the elastically deformable convoluted tip portion.

13. The device according to claim 11, wherein the deformation is configured to result in a change in length of the elastically deformable convoluted tip portion.

14. A device designed for multiple uses and sterilizations up to a preset limit, comprising:
    an elongate body, wherein the elongate body comprises a distal end and a proximal end, wherein the distal end comprises a distal tip connected to the elongate body, and further wherein the distal tip comprises a first flexible convoluted electroformed metal shell and the elongate body comprises a second flexible convoluted electroformed metal shell, wherein the first and second flexible convoluted electroformed shells are substantially hermetic;
    a control handle located at the proximal end of the elongate body for manipulating the device;

wherein the device is operably connected to an integrated circuit chip configured to determine the number of past uses already consumed and permits further usages up to said preset limit; and wherein the first flexible convoluted electroformed metal shell is more flexible than the second flexible convoluted electroformed metal shell.

\* \* \* \* \*